United States Patent
Marino et al.

(10) Patent No.: US 6,251,140 B1
(45) Date of Patent: Jun. 26, 2001

(54) INTERLOCKING SPINAL INSERTS

(75) Inventors: James F. Marino, La Jolla; Dan K. Ahlgren, San Diego, both of CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/320,236

(22) Filed: May 26, 1999

Related U.S. Application Data

(60) Provisional application No. 60/086,945, filed on May 27, 1998, provisional application No. 60/113,651, filed on Dec. 23, 1998, and provisional application No. 60/120,663, filed on Feb. 19, 1999.

(51) Int. Cl.[7] .................................................. A61F 2/44
(52) U.S. Cl. ...................................... 623/17.16; 623/17.11
(58) Field of Search .............................. 623/17.11, 17.12, 623/17.13, 17.14, 17.15, 17.16, 16.11, 11.11

(56) References Cited

U.S. PATENT DOCUMENTS

| | | |
|---|---|---|
| 3,745,995 | 7/1973 | Kraus . |
| 3,848,601 | 11/1974 | Ma et al. . |
| 4,026,304 | 5/1977 | Levy . |

(List continued on next page.)

FOREIGN PATENT DOCUMENTS

| | | |
|---|---|---|
| 2015507 | 6/1991 | (CA) . |
| 0706876 | 4/1996 | (EP) . |
| 0716840 | 6/1996 | (EP) . |
| 0517030 | 9/1996 | (EP) . |
| 0737448 | 10/1996 | (EP) . |
| 0796593 | 9/1997 | (EP) . |
| 0809974 | 12/1997 | (EP) . |
| 0809975 | 12/1997 | (EP) . |
| 0811356 | 12/1997 | (EP) . |
| 0369603 | 5/1998 | (EP) . |
| 880938 | 12/1998 | (EP) . |
| WO 91/06261 | 5/1991 | (WO) . |
| WO 94/04100 | 3/1994 | (WO) . |
| WO 94/10928 | 5/1994 | (WO) . |
| WO 95/01810 | 1/1995 | (WO) . |
| WO 96/08205 | 3/1996 | (WO) . |
| WO 96/17564 | 6/1996 | (WO) . |
| WO 96/41582 | 12/1996 | (WO) . |
| WO 97/20513 | 6/1997 | (WO) . |
| WO 97/33525 | 9/1997 | (WO) . |
| WO 97/37620 | 10/1997 | (WO) . |
| WO 98/09586 | 3/1998 | (WO) . |
| WO 98/14142 | 4/1998 | (WO) . |
| WO 98/17208 | 4/1998 | (WO) . |
| WO 99/08627 | 2/1999 | (WO) . |
| WO 99/38461 | 8/1999 | (WO) . |

OTHER PUBLICATIONS

McCord et al., "Anterior endoscopic thoracolumbar instrumentation" ActroMed® Corporation, 3303 Carnegie Avenue, Cleveland, OH, 44115 (1996) pp. 1–16.

Kambin et al., "History and current status of percutaneous arthroscopic disc surgery" *Spine* (1996) 21(24S):57S–61S.

Cargill et al., "Current and future approaches to lumbar disc surgery: A literature review" *Medscape Orthopedics & Sports Medicine,* http://www.medscape.com/Medscape/OrthoSportsMed/1997/v01.n11/m.../mos3057.alleyne.html (printed from Wolrd Wide Web: Mar. 15, 1998) 20 pages total.

*Primary Examiner*—David H. Willse
*Assistant Examiner*—Alvin Stewart
(74) *Attorney, Agent, or Firm*—Townsend and Townsend and Crew LLP

(57) ABSTRACT

A method of interlocking first and second inserts between adjacent vertebrae comprising: introducing the first insert between adjacent vertebrae; rotating the first insert to anchor the first insert into a fixed position between the adjacent vertebrae; introducing the second insert between the adjacent vertebrae; rotating the second insert to anchor the second insert into a fixed position between the adjacent vertebrae; and fastening the first insert to the second insert.

24 Claims, 7 Drawing Sheets

U.S. PATENT DOCUMENTS

| | | | |
|---|---|---|---|
| 4,657,550 | * 4/1987 | Daher | 623/17 |
| 4,781,591 | 11/1988 | Allen . | |
| 4,877,020 | 10/1989 | Vich . | |
| 4,932,975 | 6/1990 | Main et al. . | |
| 4,961,740 | 10/1990 | Ray et al. . | |
| 5,026,373 | 6/1991 | Ray et al. . | |
| 5,055,104 | 10/1991 | Ray . | |
| 5,062,845 | 11/1991 | Kuslich et al. . | |
| 5,133,717 | 7/1992 | Chopin . | |
| 5,171,278 | 12/1992 | Pisharodi . | |
| 5,290,494 | 3/1994 | Coombes et al. . | |
| 5,300,076 | 4/1994 | Leriche . | |
| 5,304,210 | 4/1994 | Crook . | |
| 5,306,307 | 4/1994 | Senter et al. . | |
| 5,306,309 | 4/1994 | Wagner et al. . | |
| 5,334,205 | 8/1994 | Cain . | |
| 5,336,223 | 8/1994 | Rogers . | |
| 5,364,400 | 11/1994 | Rego, Jr. et al. . | |
| 5,395,372 | 3/1995 | Holt et al. . | |
| 5,397,363 | 3/1995 | Gelbard . | |
| 5,413,602 | 5/1995 | Metz-Stavenhagen . | |
| 5,425,772 | * 6/1995 | Brantigan | 623/17 |
| 5,443,514 | 8/1995 | Steffee . | |
| 5,443,515 | 8/1995 | Cohen et al. . | |
| 5,445,639 | 8/1995 | Kuslich et al. . | |
| 5,454,811 | 10/1995 | Huebner . | |
| 5,458,638 | 10/1995 | Kuslich et al. . | |
| 5,489,308 | 2/1996 | Kuslich et al. . | |
| 5,522,879 | 6/1996 | Scopelianos . | |
| 5,522,899 | 6/1996 | Michelson . | |
| 5,524,624 | 6/1996 | Tepper et al. . | |
| 5,534,030 | 7/1996 | Navarro et al. . | |
| 5,540,688 | 7/1996 | Navas . | |
| 5,562,736 | 10/1996 | Ray et al. . | |
| 5,565,005 | 10/1996 | Erickson et al. . | |
| 5,571,192 | 11/1996 | Schönhöffer . | |
| 5,593,409 | 1/1997 | Michelson . | |
| 5,609,636 | 3/1997 | Kohrs et al. . | |
| 5,611,800 | 3/1997 | Davis et al. . | |
| 5,645,598 | 7/1997 | Brosnahan et al. . | |
| 5,653,761 | 8/1997 | Pisharodi . | |
| 5,653,762 | 8/1997 | Pisharodi . | |
| 5,658,336 | 8/1997 | Pisharodi . | |
| 5,658,337 | 8/1997 | Kohrs et al. . | |
| 5,665,122 | 9/1997 | Kambin . | |
| 5,669,909 | 9/1997 | Zdeblick et al. . | |
| 5,676,703 | 10/1997 | Gelbard . | |
| 5,683,394 | 11/1997 | Rinner . | |
| 5,683,464 | 11/1997 | Wagner et al. . | |
| 5,690,629 | 11/1997 | Asher et al. . | |
| 5,700,264 | 12/1997 | Zuckerman et al. . | |
| 5,700,291 | 12/1997 | Kuslich et al. . | |
| 5,700,292 | 12/1997 | Margulies . | |
| 5,702,449 | 12/1997 | McKay . | |
| 5,702,451 | 12/1997 | Biedermann et al. . | |
| 5,702,453 | 12/1997 | Rabbe et al. . | |
| 5,711,957 | 1/1998 | Patat et al. . | |
| 5,716,415 | 2/1998 | Steffee . | |
| 5,720,748 | 2/1998 | Kuslich et al. . | |
| 5,766,252 | * 6/1998 | Henry et al. | 623/17 |
| 5,772,661 | 6/1998 | Michelson . | |
| 5,785,710 | 7/1998 | Michelson . | |
| 5,797,909 | 8/1998 | Michelson . | |
| 5,800,550 | 9/1998 | Sertich . | |
| 5,814,084 | 9/1998 | Grivas et al. . | |
| 5,885,299 | 3/1999 | Winslow et al. . | |
| 5,888,224 | * 3/1999 | Beckers et al. | 623/17 |
| 5,893,890 | * 4/1999 | Pisharodi | 623/17 |
| 5,968,098 | 10/1999 | Winslow . | |
| 6,004,326 | 12/1999 | Castro et al. . | |
| 6,015,436 | * 1/2000 | Schunhuffer | 623/17 |
| 6,033,405 | 3/2000 | Winslow et al. . | |
| 6,039,761 | * 3/2000 | Li et al. | 623/17 |
| 6,042,582 | 3/2000 | Ray . | |
| 6,063,088 | 5/2000 | Winslow . | |
| 6,083,225 | 7/2000 | Winslow et al. . | |
| 6,102,948 | 8/2000 | Brosnahan, III . | |
| 6,120,506 | 9/2000 | Kohrs et al. . | |

\* cited by examiner

INTERLOCKING SPINAL INSERTS

CROSS-REFERENCES TO RELATED APPLICATIONS

The present application is a regular application of U.S. Provisional Patent Application Ser. No. 60/086,945 filed May 27, 1998; U.S. Provisional Patent Application No. 60/113,651 filed Dec. 23, 1998; and No. 60/120,663 filed Feb. 19, 1999; the complete disclosure of which are hereby incorporated herein by reference for all purposes.

TECHNICAL FIELD

The present invention relates to intervertebral spinal inserts.

BACKGROUND OF THE INVENTION

Intervertebral spinal inserts are used to provide support and maintain normal distance between adjacent vertebrae in cases where a patient's vertebral discs have degenerated. Such degeneration can occur as a result of aging or trauma and typically results in pinched or damaged nerves between or proximal to the adjacent vertebrae. Moreover, such discal degeneration causes shifting of the loading along the patient's spinal column, which in turn further accelerates the vertebral degeneration.

Intervertebral inserts are typically used to reestablish normal intervertebral spacing and to cause fusion between adjacent vertebral bodies.

A common problem with the existing intervertebral spinal inserts is that they do not provide stabilization in two perpendicular directions in the plane of the patient's intervertebral space.

Another disadvantage is that, during such major surgery, the actual insertion of the intervertebral insert requires distraction of the adjacent vertebrae to first open a sufficiently large passage for the insertion of the insert therebetween. Such distraction is typically performed by dedicated instrumentation and invasive tools which must first enter the intervertebral space and then grip and hold apart the adjacent vertebrae.

Moreover, the shape of current inserts does not take advantage of the natural contoured shape of the adjacent vertebral surfaces such that an intervertebral insert can be provided which supports itself flush against the contour of the vertebral surfaces with the vertebrae being supported at a proper lordotic angle.

SUMMARY OF THE INVENTION

In a preferred aspect of the present invention, first and second intervertebral inserts are positioned in a patient's intervertebral space between adjacent vertebrae. The inserts are positioned parallel to the vertebrae with their central longitudinally extending axes disposed at an angle to one another. Preferably, the angle between central longitudinally extending axes of the inserts ranges from 70° to 135° and is most preferably about 90°. Due to the fact that the inserts have their central longitudinally extending axes oriented generally perpendicular to one another, increased vertebral stability is provided. An advantage of such increased stability is that the potential for vertebral fusion is increased.

In addition, the inserts are interlocked together with one another, enhancing their stability. Preferably, the inserts are each sequentially rotated about their respective central longitudinally extending axes into an anchored position between the adjacent vertebrae such that teeth on each of the inserts penetrates into the surfaces of the vertebrae, securing the inserts into position. In preferred aspects of the invention, the rotation of the inserts causes the inserts to become interlocked together, such that relative motion therebetween is prevented.

In preferred aspects of the invention, each of the first and second interlocking inserts have opposite outwardly facing convexly curved camming surfaces thereon, which act to cam apart the adjacent vertebrae when the inserts are rotated into an anchored position. Specifically, the outwardly facing convexly curved camming surfaces are adapted to engage, and to separate by camming action, the opposed adjacent vertebrae when the insert is initially placed between the vertebrae and then subsequently rotated by 90°. An illustration of employing such outwardly facing convexly curved camming surfaces to cam apart the adjacent vertebrae is provided in provisional patent applications Ser. No. 60/086,945 filed May 27, 1998; No. 60/113,651 filed Dec. 23, 1998; and No. 60/120,663 filed Feb. 19, 1999; incorporated herein by reference in their entirety. After the inserts are rotated into position, they support the spinal load, thereby easing pressure on the vertebral disc and surrounding tissue. As such, prior distraction of the adjacent vertebrae with dedicated instrumentation is either not required, or is substantially minimized.

In preferred aspects of the invention, the first and second inserts are each positioned within the patient's intervertebral space by separate cannulae entering the patient in opposite posterolateral approaches. Preferably, the cannulae are introduced percutaneously through the patient's back at generally right angles to one another. The inserts are preferably advanced through the respective cannulae into the intervertebral area in a fluoroscopically guided approach. Since the first and second inserts are inserted and anchored into position by the present method with only two percutaneous cannulae being required, a very minimally invasive surgical technique is provided.

This minimally invasive approach offers the benefit of introducing each insert while avoiding damage to the anterior and posterior longitudinal ligaments, interspinous ligaments and the facet joint capsules, while enabling the positioning of the inserts at generally right angles to one another with each insert being at an angle of about 45° to the sagittal plane of the patient.

In further preferred aspects of the method, the cannulae have an oval, racetrack, or other non-symmetric cross-section such that the cross-sectional area is substantially reduced from that of a generally circular cross-sectional cannula, reducing patient trauma and facilitating accurate placement fully into the patient's intervertebral space when the cannula is received into the patient.

In a preferred aspect, the size and shape of the insert creates a proper lordotic angle between the adjacent vertebrae. Specifically, in a preferred aspect, the insert has opposite, flattened vertebral support surfaces which taper inwardly towards the rotational axis at the posterior end of the insert. Optionally, the vertebral support surfaces can also be angled with respect to one another across the insert in a direction perpendicular to the central longitudinal axis of the insert. This tapering and angling of the vertebral support surfaces permits the insert to provide the required lordosis angle along the anterior-posterior contour of the opposite adjacent vertebrae.

In another aspect of the present invention, the insert is fabricated from a bio-absorbable material such that it will eventually be absorbed into the patient's body over time. For example, in a preferred aspect, the material used would be poly-L-lactic acid, polyglycolic acid, collagen, calcium phosphates, bioabsorbable ceramics, or any combination thereof which imparts sufficient initial implant strength to distract the vertebral bodies, to maintain a preferred vertebral spacing for a period of time, and which would be resorbed thereafter to promote natural disc healing. By varying the composition of the bio-absorbable material, the speed of bio-absorption can be adjusted per the desired use of the insert.

DEFINITIONS

As used herein, the following terms are understood to have the following meanings:

"camming"—increasing intervertebral separation by rotating opposite convexly curved sides of an intervertebral insert against adjacent vertebrae.

"distraction"—pulling apart, separating, or increasing the distance between adjacent opposite vertebrae by physical or mechanical means.

"fusion"—complete ingrowth of bone tissue between adjacent vertebrae.

"outwardly facing convexly curved camming surface"—a surface having a degree of curvature corresponding to an arc section defined by an angle in the range of 15 to 40 degrees, and most preferably about 20 degrees.

"posterolateral"—behind and to one side.

"—racetrack-shaped"—a shape having two elongated parallel sides and two curved ends.

DESCRIPTION OF THE SPECIFIC EMBODIMENTS

Figure 1:
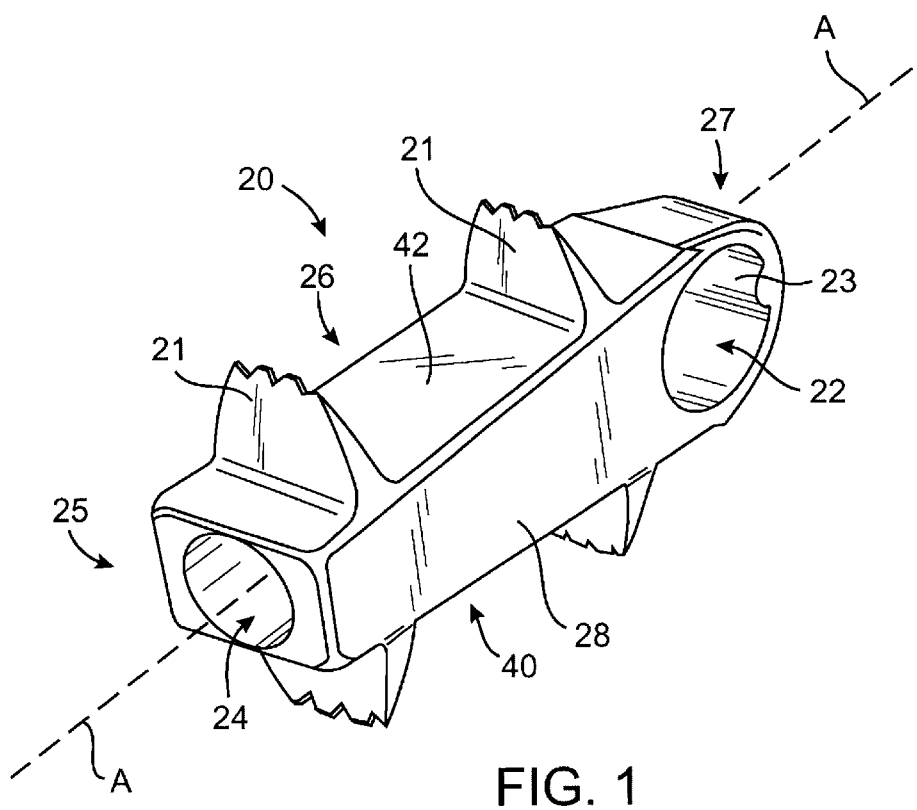
FIG. 1 is a rear perspective view of the first insert.
Figure 2:
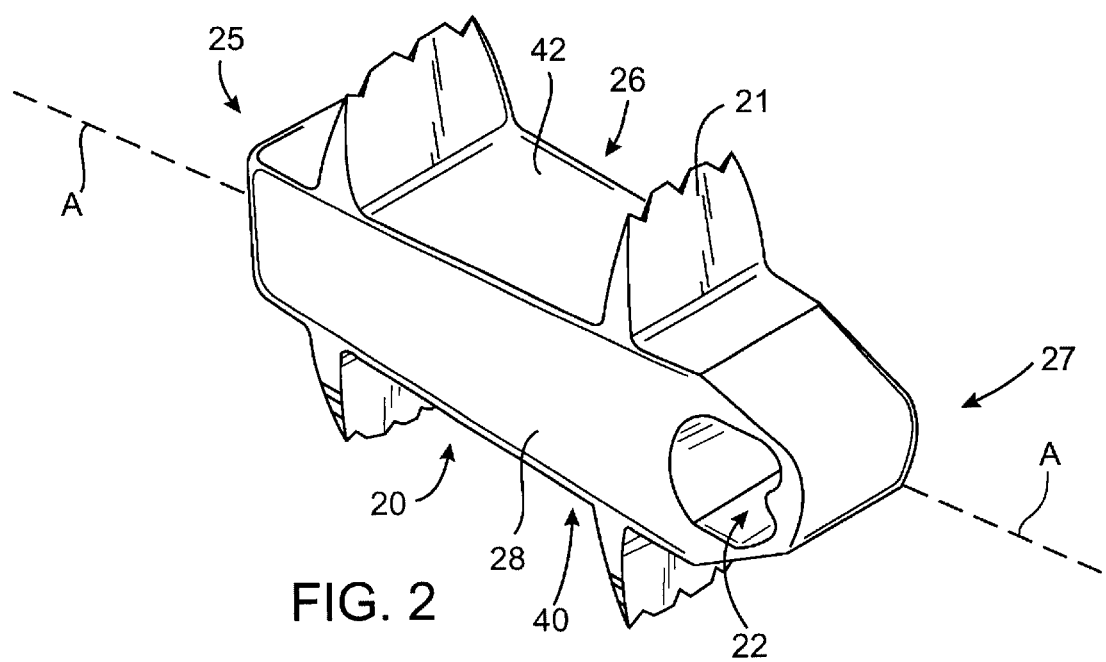
FIG. 2 is a front perspective view of the first insert.

As seen in FIGS. 1 and 2, a first insert 20 is provided. Insert 20 has a posterior end 25, an anterior end 27 and a longitudinally extending central rotational axis A passing therebetween.

Figure 3:
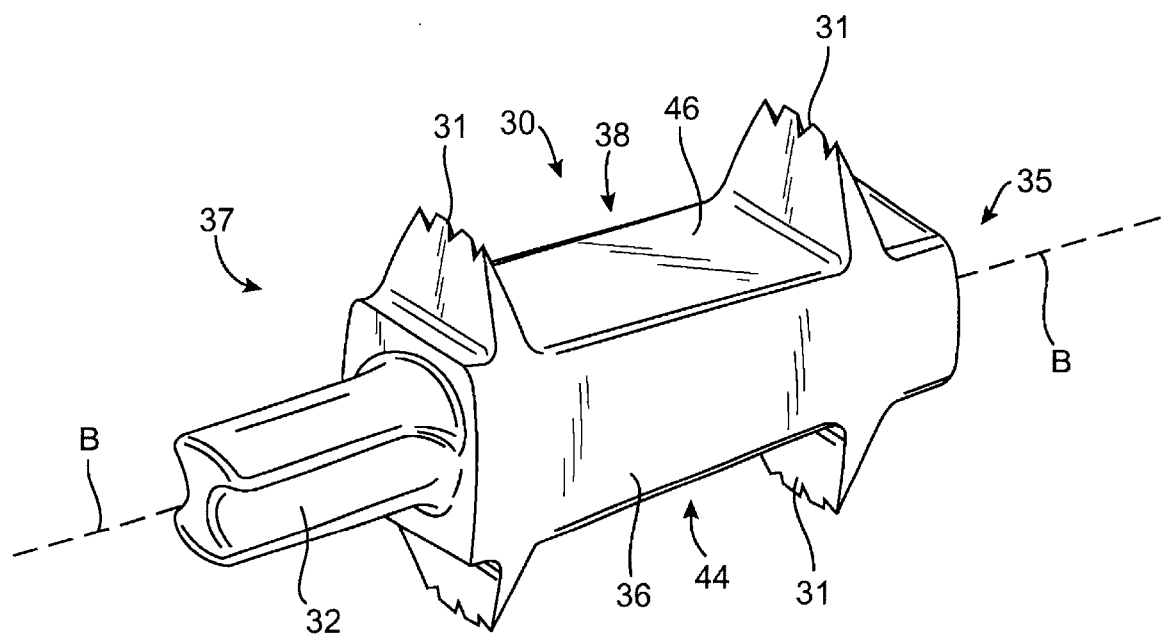
FIG. 3 is a rear perspective view of the second insert.
Figure 4:
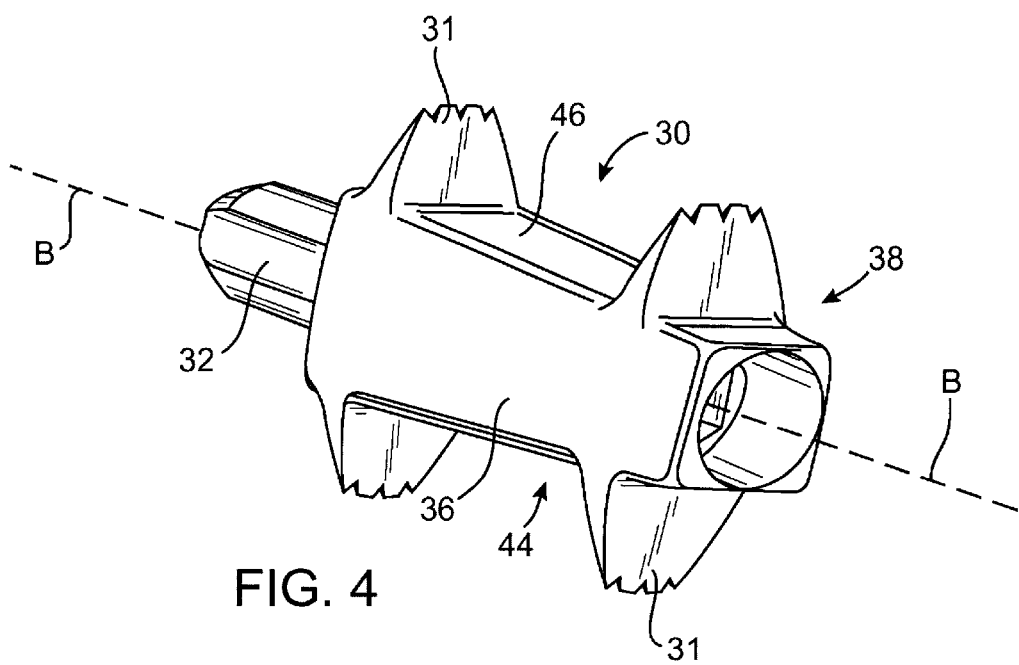
FIG. 4 is a front perspective view of the second insert.

As seen in FIGS. 3 and 4, a second insert 30 is provided. Insert 30 has a posterior end 35, an anterior end 37 and a longitudinally extending central rotational axis B passing therebetween.

To provide optimal intervertebral support, the length of each of inserts 20 and 30 (i.e., the separation distance between ends 25 to 27 and 35 to 37 respectively) is in the range of 15 to 30 mm, and is most preferably about 25 mm.

In a preferred aspect of the invention, a pair of outwardly facing surfaces 26 and 28 are disposed on opposite sides of insert 20 as shown. In one aspect of the invention, (as seen in FIGS. 2 and 4), surfaces 26 and 28 and 36 and 38 are generally planar. In an alternate aspect of the invention, (shown in FIG. 6 for insert 30 and FIG. 9 for insert 20), surfaces 36, 38, 26 and 28 are convexly curved camming surfaces. Similarly, surfaces 26 and 28 may be convexly curved camming surfaces.

In either planar or curved embodiments, surfaces 26, 28, 36 and 38 are adapted to engage, and to separate by camming action, the opposed vertebral surfaces when insert 20 or 30 is placed between adjacent vertebrae and rotated by 90° into an anchored position, as will be described. In a preferred aspect, as fully described in provisionally filed patent application Ser. No. 60/086,945 filed May 27, 1998; No. 60/113,651 filed Dec. 23, 1998; and No. 60/120,663 filed Feb. 19, 1999; incorporated herein by reference in their entirety, surfaces 26, 28, 36 and 38 dimensioned to represent an arc segment in the range of 15 to 40 degrees, and is most preferably about 20 degrees. It is to be understood, however, that the degree of curvature of surfaces 26, 28, 36 and 38 is not limited by the present invention and that the present invention comprises flatter are more rounded surfaces.

As can be seen in FIGS. 1 to 4, opposite flattened vertebral contact surfaces 40 and 42 (on insert 20) and 44 and 46 (on insert 30) are disposed between outwardly facing convexly surfaces 26 and 28 (on insert 20) and 36 and 38 (on insert 30). As will be explained in conjunction with a preferred method described herein, opposite flattened surfaces 40, 42, 44 and 46 are adapted to provide a flush contact against and thereby buttress adjacent separated vertebrae 50 and 52 after respective inserts 20 and 30 have been rotated into position.

Figure 6:
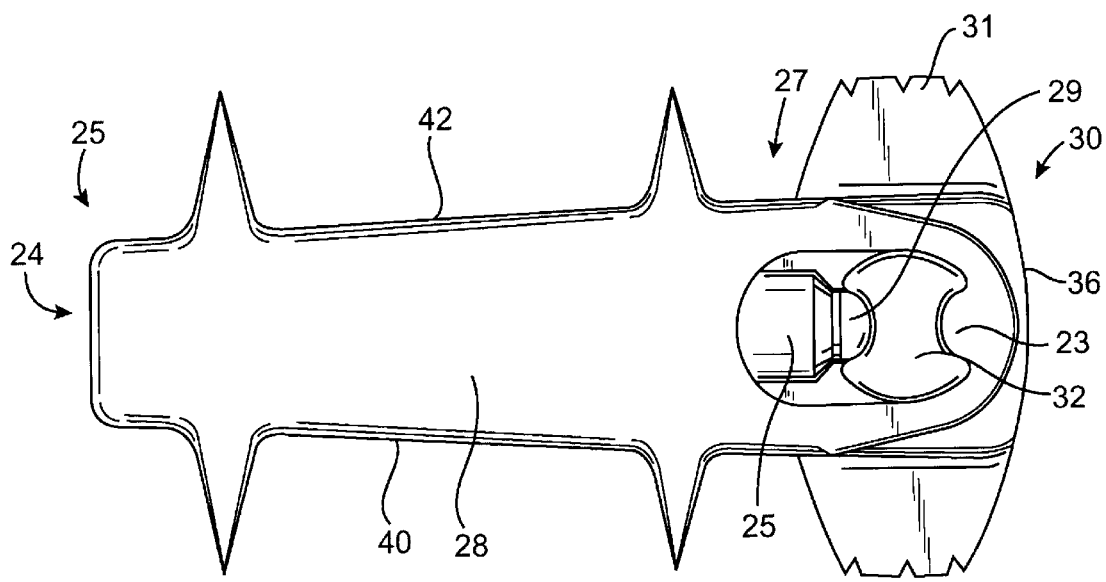
FIG. 6 is a side elevation view of the interlocking inserts showing a side of the first insert and an end of the second insert.

Preferably, as seen in FIG. 6, vertebral support surfaces 40 and 42 (on insert 20) are angled with respect to one another to taper from a short posterior end 25 to a tall anterior end 27. Similarly, vertebral support surfaces 44 and 46 (on insert 30) may be angled with respect to one another to taper from a short posterior end 35 to a tall anterior end 37. The tapering of inserts 20 and 30 from tall anterior ends 27 and 37 to short posterior ends 25 and 27 supports the adjacent vertebrae at a required lordosis angle when the inserts are positioned therebetween.

Figure 7:
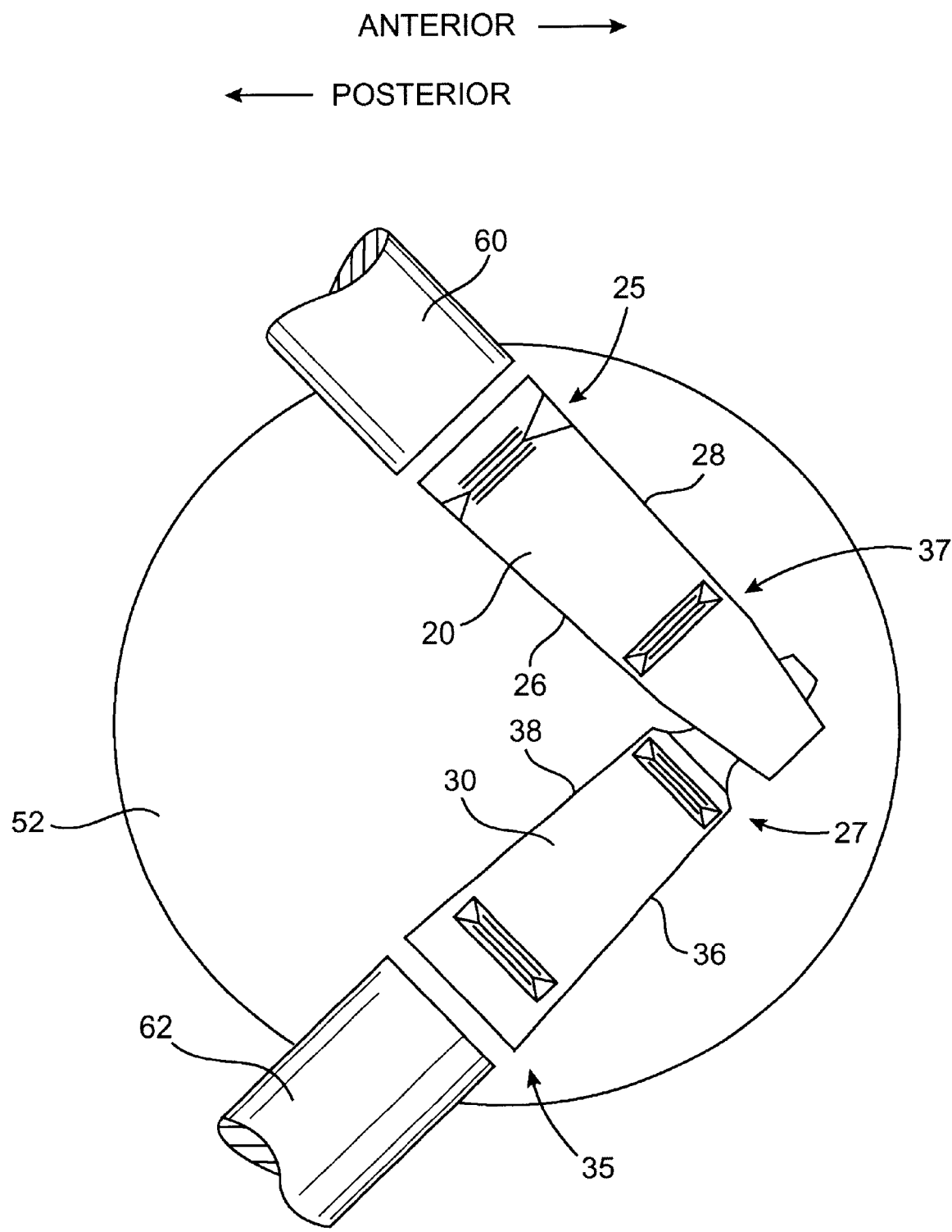
FIG. 7 is a top plan view of the interlocking first and second inserts, in an anchored position between adjacent vertebrae, (with the top vertebra removed for illustration clarity).

Optionally, as seen in FIG. 7, outwardly facing surfaces 26 and 28 (on insert 20) and 36 and 38 (on insert 30) may be angled with respect to one another to taper from wide posterior ends 25 and 35 to narrow anterior ends 27 and 37, facilitating intervertebral insertion. In particular, the angling of surfaces 26 and 28 (on insert 20) and 36 and 38 (on insert 30) results in a tapered shape for inserts 20 and 30 from a narrow anterior ends 27 and 37 to wide posterior ends 25 and 35, which facilitates vertebral distraction when the insert is first introduced between the vertebrae, even prior to its rotation. Specifically, when the respective insert is introduced into the vertebral space in a posterior approach, narrow anterior end 27 or 37 is introduced first, operating as a wedge to separate the adjacent vertebrae, as the insert is received therebetween.

As is seen in FIGS. 1 to 4, anchoring fins 21 and 31 extend outwardly from each of opposite vertebral support surfaces 40 and 42 (on insert 20) and 44 and 46 (on insert 30).

Optionally, fins 21 and 31 may be textured on their projecting edges and expanded at their bases so as to increase their ability to penetrate the vertebral endplates and enhance vertebral stability. Optionally, fins 21 and 31 may be barbed so as to increase their ability to remain firmly secured into the opposite adjacent vertebral surfaces.

Figure 8A:
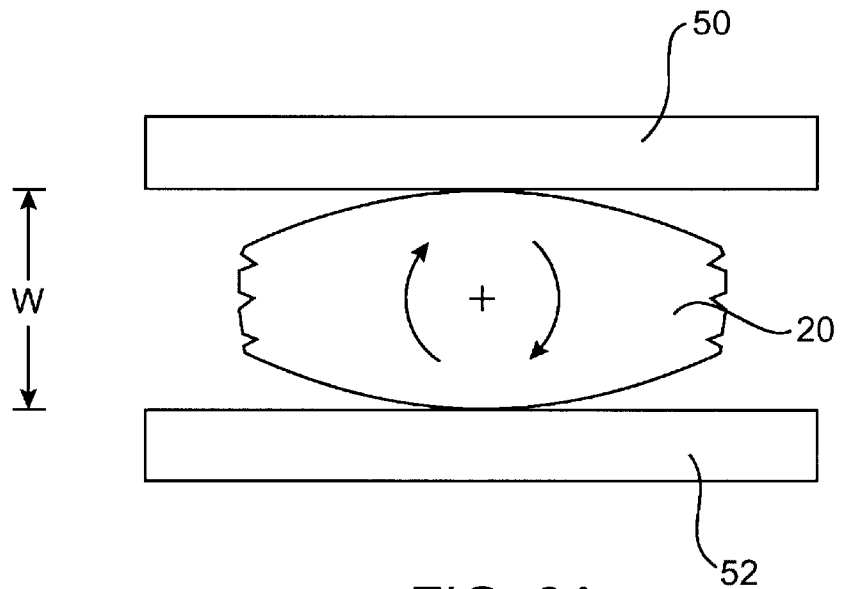
FIGS. 8A and 8B are successive illustrations of a first insert being rotated into an anchored position between adjacent vertebrae.

The preferred method of inserting each of inserts 20 and 30 between adjacent vertebrae 50 and 52 is fully described in provisionally filed patent application Ser. No. 60/086,945 filed May 27, 1998; No. 60/113,651 filed Dec. 23, 1998; and No. 60/120,663 filed Feb. 19, 1999; incorporated herein by reference in their entirety. The preferred method is also illustrated in the sequential drawings of FIGS. 8A and 8B. As will be explained, each of inserts 20 and 30 are inserted in sequence using this method. FIG. 8A illustrates the initial insertion of insert 20 between adjacent vertebrae 50 and 52. Insert 20 is rotated by 90° (to the position shown in FIG. 8B), to separate and stabilize adjacent vertebrae 50 and 52 by engaging outwardly facing surfaces 26 and 28 (which may preferably be convexly curved) to cam apart vertebrae 50 and 52, anchoring insert 20 with teeth 21 secured into adjacent vertebrae 50 and 52. Having a small width W in relation to its height H, insert 20 can easily be inserted between the adjacent vertebrae with minimal or no prior distraction of the vertebrae, which would require highly invasive distractor tools being first inserted.

Specifically, when rotating insert 20 into position, camming surfaces 26 and 28 operate to smoothly cam apart vertebrae 50 and 52, and flattened vertebral contact surfaces 40 and 42 become flush with the surfaces of vertebrae 50 and 52, thereby providing a stable buttressing support between the adjacent vertebrae, as anchoring fins 21 protrude therein.

Figure 5:
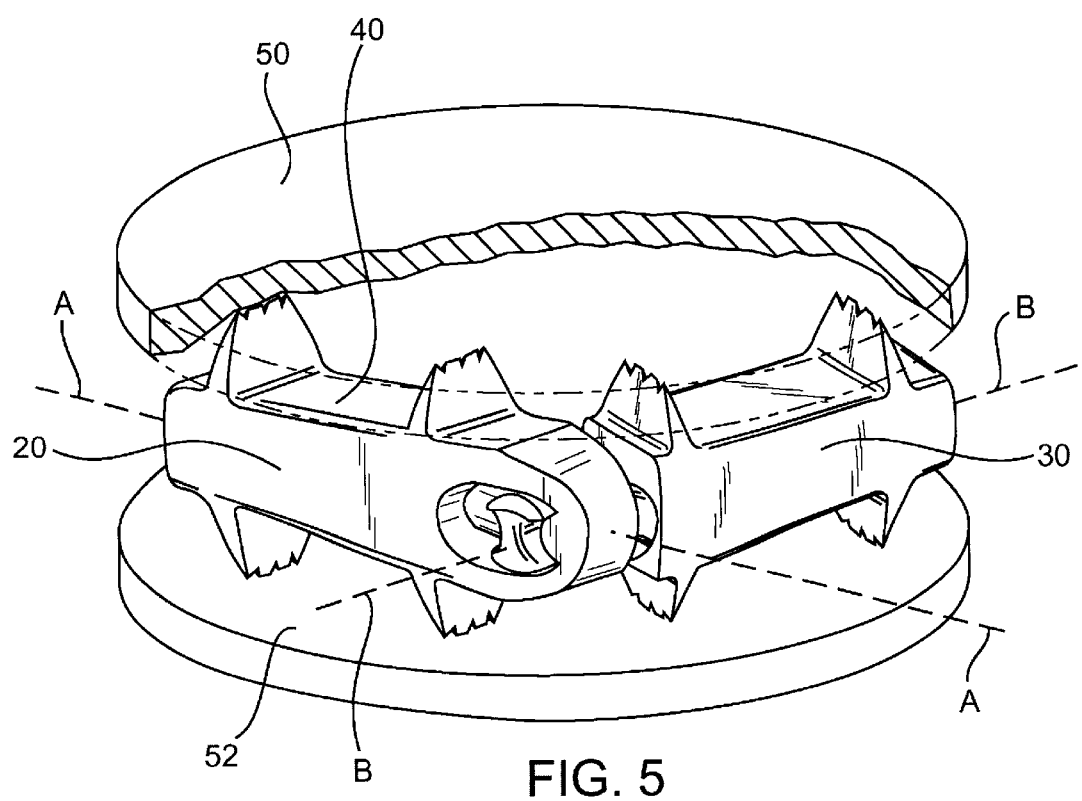
FIG. 5 is an exploded front perspective view of first and second interlocking intervertebral inserts, interlocked together and anchored into position between adjacent vertebrae.

FIG. 5 shows an illustration of the positioning of the interlocked inserts, exploded to show vertebrae 50 and 52 positioned thereover and thereunder. As seen in FIG. 5, inserts 20 and 30 can be interlocked together, thereby providing support between adjacent vertebrae 50 and 52. Being disposed with their rotational axes A and B at an angle of 90° to one another in the plane between vertebrae 50 and 52, inserts 20 and 30 offer increased vertebral stability to the patient since their central axes A and B are generally perpendicular.

Figure 8B:
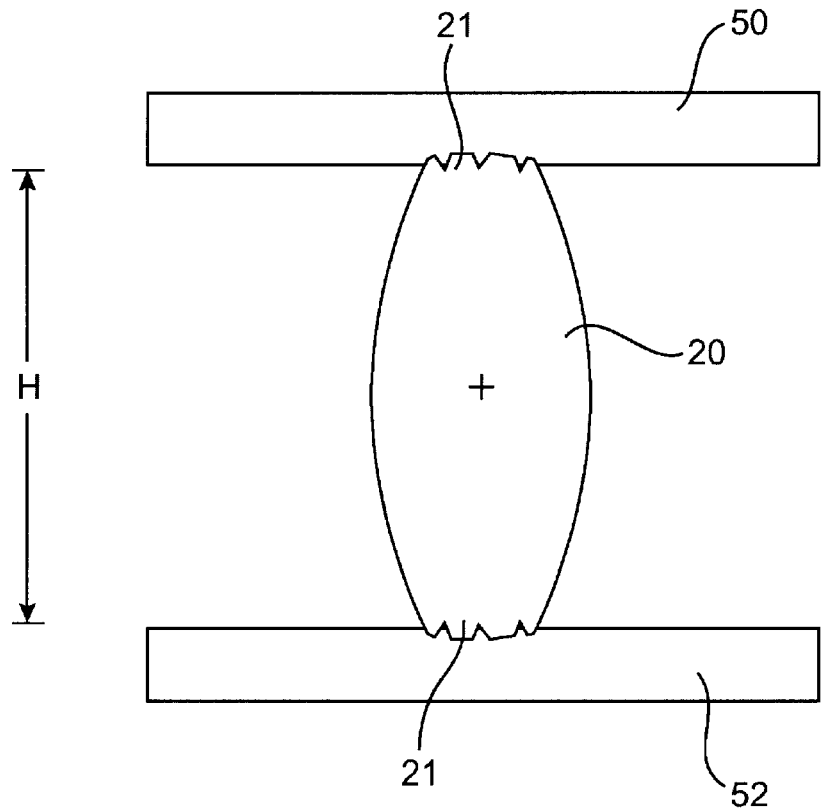

Inserts 20 and 30 may be interlocked together using a variety of techniques. For example, referring to FIG. 7, insert 20 can be first received into the patient's intervertebral space by being passed through a percutaneously inserted cannula 60. When initially received into the patient's intervertebral space, insert 20 is positioned on its side with its teeth 21 disposed between adjacent vertebrae 50 and 52, as shown in FIG. 8A. Subsequent to placement in the intervertebral space, insert 20 is then rotated by 90 degrees about axis A such that teeth 21 penetrate into the surfaces of vertebrae 50 and 52 respectively, thereby anchoring insert 20 into position, as is shown in FIG. 8B.

Subsequently, using the same camming method, insert 30 is similarly received into the intervertebral space, preferably by being passed through a second percutaneously inserted cannula 62, as shown in FIG. 7. As can be seen, the first and second cannulae 60 and 62 are preferably angled at 90 degrees to one another such that inserts 20 and 30 at also angled at 90 degrees to one another.

Insert 30 is then rotated by 90 degrees about its central longitudinal axis B such that its teeth 31 penetrate into the surfaces of vertebrae 50 and 52, locking insert 30 into position between the vertebrae.

As is seen in FIGS. 3 and 4, insert 30 has a dog bone shaped projection 32 which is received into hole 22 in insert 20. As insert 30 is rotated by 90° into position such that teeth 31 anchor into vertebrae 50 and 52 respectively, projection 32 will rotate in hole 22 such that it rests against stub 23.

A threaded hole 24 longitudinally extending through insert 20 is also provided. A screw type fastener 25 is disposed within hole 24 such that when advanced along the internal threading, a protrusion 29 on fastener 25 is advanced against protrusion 32, thereby locking insert 20 and 30 together in a perpendicular orientation, as shown.

Figure 9:
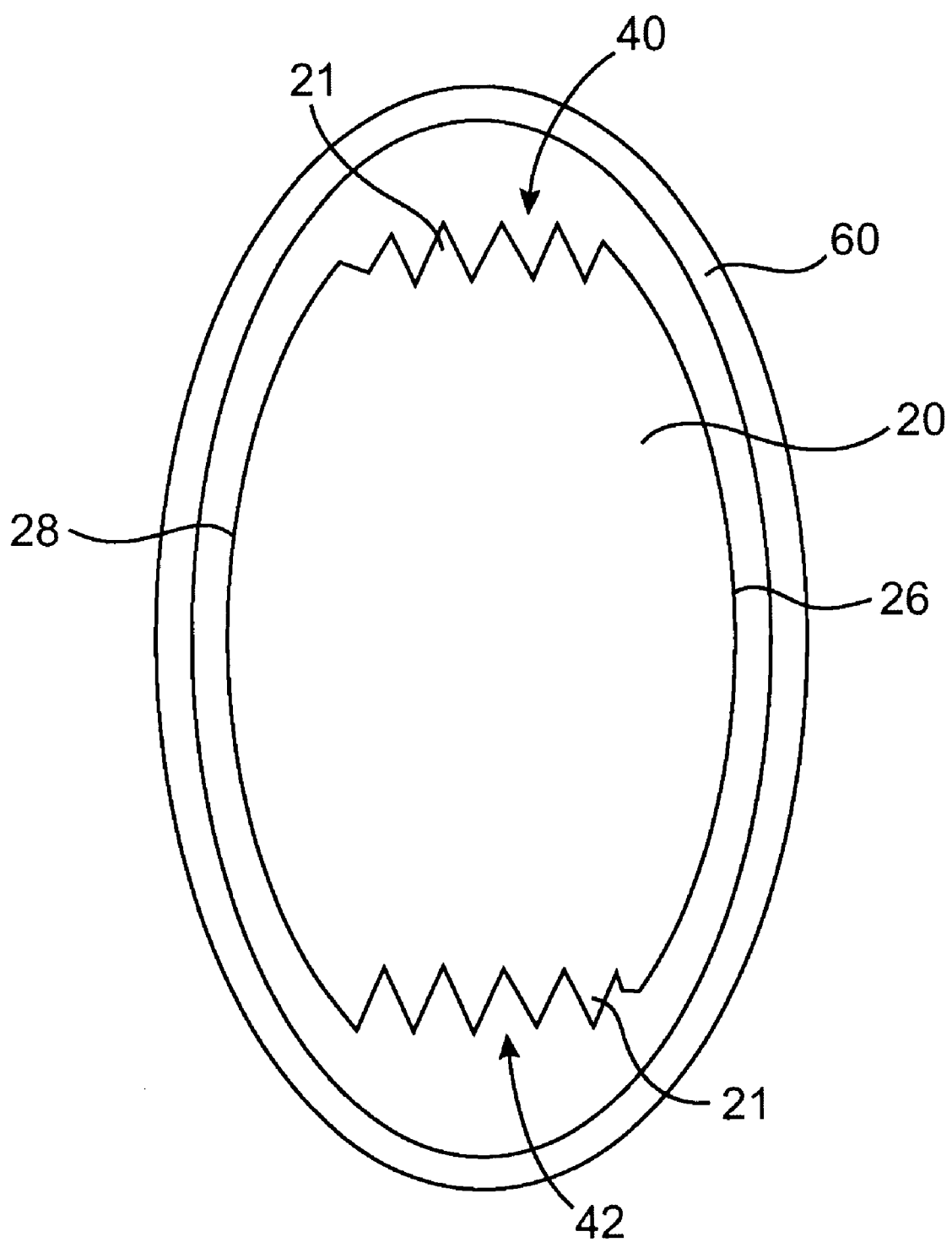
FIG. 9 is a an end view of a first insert received in an oval-shaped cannula.

Inserts 20 and 30 are each ideally adapted for delivery through a cannula having a non-symmetric cross-section which may be used for percutaneously introducing the insert with a minimal amount of tissue disruption. As is shown in FIG. 9, (which illustrates an end view of insert 20 in cannula 60), the non-symmetric cannula can have an oval or racetrack-shaped lumen 45 shaped to slidingly mate with opposite outwardly facing convexly camming surfaces 26 and 28 of insert 20, thereby preventing insert 20 from rotating while in cannula 60. The use of cannula 60 permits insert 20 to be introduced percutaneously with minimal invasion and surrounding tissue damage as its flattened elongated cross-sectional shape permits it to be easily received between the adjacent vertebrae 50 and 52.

Optionally, vertebral contact surfaces 40 and 42 of implant 20 (and 44 and 46 of insert 30) can also be angled with respect to one another across the width of the inserts in a direction perpendicular to central longitudinal axes A and B such that they assist in providing proper lordosis between the adjacent vertebrae when two inserts are positioned at right angles to one another in the intervertebral space.

FIG. 7 illustrates the preferred arrangement of interlocked inserts 20 and 30 with the inserts interlocking together towards the anterior side of the patient's intervertebral space.

Figure 10:
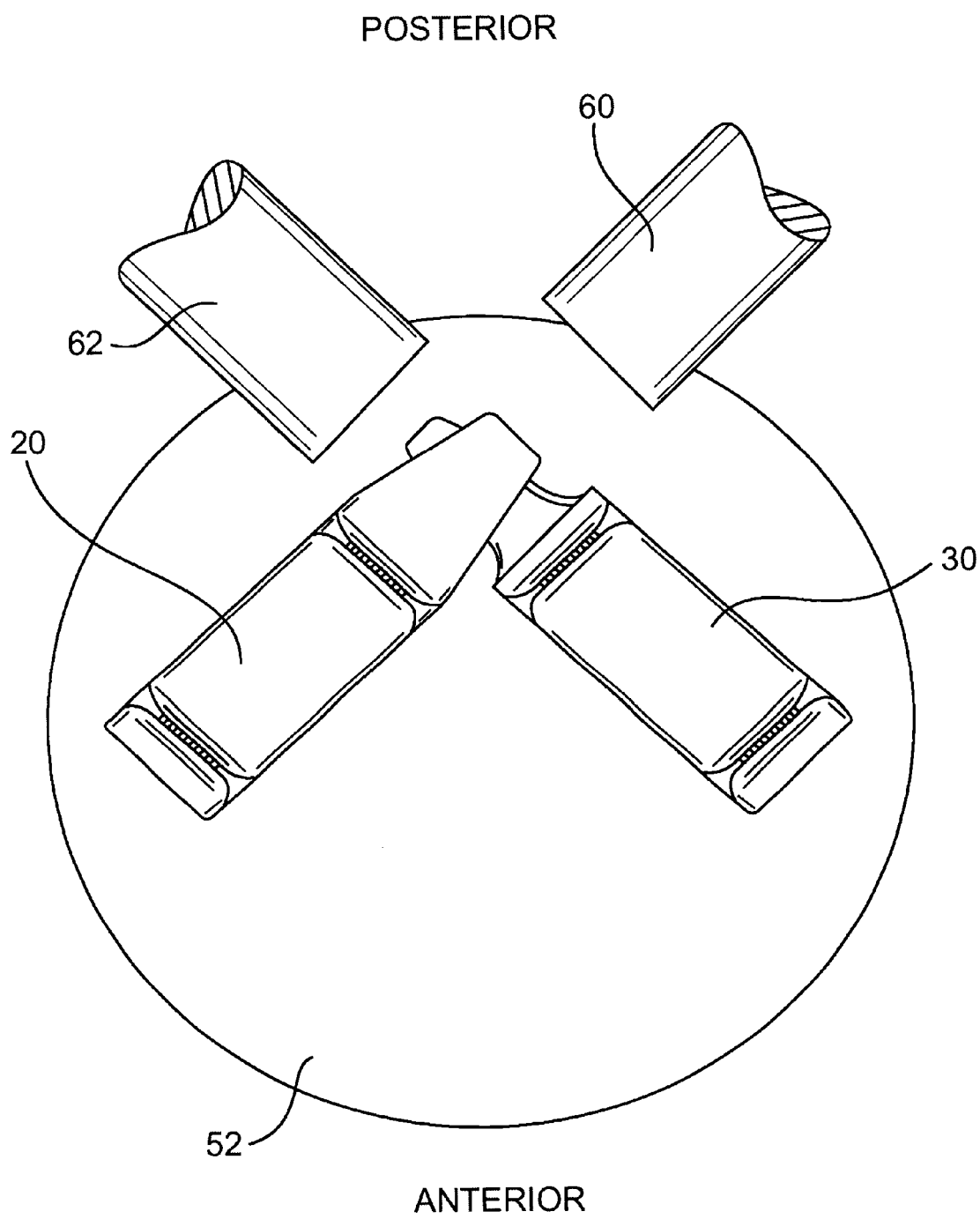
FIG. 10 is a view corresponding to FIG. 7, but with the inserts instead interlocking together towards the posterior end of the patient's intervertebral space.

FIG. 10 illustrates an alternative approach in which posterolateral cannular 60 and 62 are used to position inserts 20 and 30 to interlock together at the posterior side of the patient's intervertebral space. When positioning cannulae 60 and 62 as shown in FIG. 10, insert 30 is first preferably advanced sufficiently far into the intervertebral space such that insert 20 can be advanced into the intervertebral space without contacting insert 30. Insert 30 is then drawn back (opposite to the direction in which it was inserted), such that protrusion 32 on insert 30 advanced into hole 22 of insert 20.

What is claimed is:

1. A method of interlocking first and second inserts in a patient's intervertebral space between adjacent vertebrae comprising:
    introducing the first insert between the adjacent vertebrae, the first insert having opposite vertebral contact surfaces;
    rotating the first insert about a first axis passing between the adjacent vertebrae in a path generally parallel to opposing ends of the adjacent vertebrae to position the vertebral contact surfaces adjacent to the adjacent vertebrae;
    introducing the second insert between the adjacent vertebrae, the second insert having opposite vertebral contact surfaces;
    rotating the second insert about a second axis disposed at an angle to the first axis to position the vertebral contact surfaces adjacent to the adjacent vertebrae, wherein, the central longitudinally extending axes of the first and second intervertebral inserts are positioned to be angled from 70 to 135° apart from one another; and
    fastening the first insert to the second insert.

2. The method of claim 1, wherein fastening the second insert into the first insert comprises:
   inserting a protrusion on the second insert into a receiving hole on the first insert,
   rotating the second insert such that the protrusion rests against a stub on the wall of the receiving hole of the first insert; and
   rotating an axially displaceable threaded screw in the first insert to contact the protrusion on the second insert, thereby holding the second insert in a fixed position relative to the first insert.

3. The method of claim 2, wherein rotating the threaded screw in the first insert comprises accessing the threaded screw by way of an axially extending passageway in the first insert.

4. The method of claim 1, wherein,
   the first and second intervertebral inserts are separately introduced into the intervertebral space between the adjacent vertebrae by percutaneously introduced cannulae, each cannula positioned in a posterolateral approach.

5. The method of claim 4, wherein,
   the central longitudinally extending axes of the first and second intervertebral inserts are positioned to be angled from 70 to 135° apart from one another.

6. The method of claim 4, wherein,
   the cannulae have oval or racetrack-shaped cross sections.

7. The method of claim 1, wherein rotating the first insert to anchor the first insert comprises:
   camming apart adjacent vertebrae with outwardly facing convexly curved camming surfaces disposed on opposite sides of the insert.

8. A spinal support system, comprising:
   a first intervertebral insert having a central longitudinally extending axis, the first insert having opposite vertebral contact surfaces; and
   a second intervertebral insert having a central longitudinally extending axis, the second insert having opposite vertebral contact surfaces, wherein the first and second intervertebral inserts interlock together to form an assembly with the central longitudinally extending axes of the first and second intervertebral inserts disposed at an angle of 70° to 135° from one another when the first and second inserts have been rotated into an interlocked position.

9. The spinal support system of claim 8, wherein,
   the first and second intervertebral inserts are interlocked together at their anterior ends.

10. The spinal support system of claim 8, wherein,
    each of the first and second intervertebral inserts have outwardly facing convexly curved camming surfaces.

11. The spinal support system of claim 8, wherein,
    the width of each of the first and second intervertebral inserts are tapered from an narrow anterior end to a wide posterior.

12. The spinal support system of claim 8, wherein,
    the height of each of the first and second intervertebral inserts are tapered from a wide anterior end to a narrow posterior end.

13. The spinal support system of claim 8, wherein,
    each of the first and second intervertebral inserts are made of a bio-compatible material.

14. The spinal support system of claim 8, wherein,
    each of the first and second intervertebral inserts are made of a bio-absorbable material.

15. A method of interlocking first and second inserts between adjacent vertebrae comprising:
    introducing the first insert between adjacent vertebrae;
    rotating the first insert to anchor the first insert into a fixed position between the adjacent vertebrae;
    introducing the second insert between the adjacent vertebrae;
    rotating the second insert to anchor the second insert into a fixed position between the adjacent vertebrae; and
    fastening the first insert to the second insert by:
       inserting a protrusion on the second insert into a receiving hole on the first insert,
       rotating the second insert such that the protrusion rests against a stub on the wall of the receiving hole of the first insert; and
       rotating an axially displaceable threaded screw in the first insert to contact the protrusion on the second insert, thereby holding the second insert in a fixed position relative to the first insert.

16. The method of claim 15, wherein rotating the threaded screw in the first insert comprises accessing the threaded screw by way of an axially extending passageway in the first insert.

17. The method of claim 15, wherein,
    the first and second intervertebral inserts are separately introduced into the intervertebral space between the adjacent vertebrae by percutaneously introduced cannulae, each cannula positioned in a posterolateral approach.

18. The method of claim 17, wherein,
    the central longitudinally extending axes of the first and second intervertebral inserts are positioned to be angled from 70 to 135° apart from one another.

19. The method of claim 17, wherein,
    the cannulae have oval or racetrack-shaped cross sections.

20. The method of claim 15, wherein rotating the first insert to anchor the first insert comprises:
    camming apart adjacent vertebrae with outwardly facing convexly curved camming surfaces disposed on opposite sides of the insert.

21. A spinal support system, comprising:
    a first intervertebral insert having a central longitudinally extending axis, the first insert having opposite vertebral contact surfaces; and
    a second intervertebral insert having a central longitudinally extending axis, the second insert having opposite vertebral contact surfaces, wherein the first and second intervertebral inserts have outwardly facing convexly curve camming surfaces and are adapted to be interlocked together such that the central longitudinally extending axes of the first and second intervertebral inserts are disposed at an angle of 70° to 135° from one another.

22. A spinal support system, comprising:
    a first intervertebral insert having a central longitudinally extending axis, the first insert having opposite vertebral contact surfaces; and
    a second intervertebral insert having a central longitudinally extending axis, the second insert having opposite vertebral contact surfaces, wherein the first and second intervertebral inserts are adapted to be interlocked together such that the central longitudinally extending axes of the first and second intervertebral inserts are disposed at an angle of 70° to 135° from one another, and wherein the width of each of the first and second intervertebral inserts are tapered from an narrow anterior end to a wide posterior.

23. A spinal support system, comprising:

a first intervertebral insert having a central longitudinally extending axis; and a second intervertebral insert having a central longitudinally extending axis, wherein the first and second intervertebral inserts are adapted to be interlocked together such that the central longitudinally extending axes of the first and second intervertebral inserts are disposed at an angle of 70° to 135° from one another, and wherein the height of each of the first and second intervertebral inserts are tapered from a wide anterior end to a narrow posterior end.

24. A spinal support system, comprising:

a first intervertebral insert having a central longitudinally extending axis; and a second intervertebral insert having a central longitudinally extending axis, wherein the first and second intervertebral inserts are adapted to be interlocked together such that the central longitudinally extending axes of the first and second intervertebral inserts are disposed at an angle of 70° to 135° from one another, and wherein each of the first and second intervertebral inserts are made of a bio-absorbable material.

* * * * *